US006589798B1

(12) United States Patent
Löfås

(10) Patent No.: US 6,589,798 B1
(45) Date of Patent: Jul. 8, 2003

(54) METHOD AND SYSTEM FOR ANALYTE DETERMINATION

(75) Inventor: Stefan Löfås, Uppsala (SE)

(73) Assignee: Biacore AB, Uppsala (SE)

( * ) Notice: Subject to any disclaimer, the term of this patent is extended or adjusted under 35 U.S.C. 154(b) by 0 days.

(21) Appl. No.: 09/330,785

(22) Filed: Jun. 11, 1999

Related U.S. Application Data

(63) Continuation of application No. PCT/SE97/02071, filed on Dec. 11, 1997.

(30) Foreign Application Priority Data

Dec. 12, 1996 (SE) ............................................ 9604575

(51) Int. Cl.[7] ............................................ G01N 33/543

(52) U.S. Cl. ....................... 436/518; 436/519; 436/517; 436/523; 436/525; 436/531; 436/533; 436/534; 436/538; 436/173; 435/7.1; 435/7.93; 435/7.94; 435/7.95; 310/311; 310/313; 310/340; 73/580; 73/587; 73/590

(58) Field of Search ................................ 436/517, 518, 436/519, 523, 525, 531, 533, 534, 538, 173; 435/7.1, 7.93, 7.95, 7.94; 310/311, 313, 340; 73/580, 587, 590

(56) References Cited

U.S. PATENT DOCUMENTS

| | | | | | |
|---|---|---|---|---|---|
| 4,246,344 | A | * | 1/1981 | Silver, III | 435/39 |
| 4,271,140 | A | | 6/1981 | Bunting | 424/1 |
| 5,242,828 | A | * | 9/1993 | Bergstrom et al. | 435/291 |
| 5,306,644 | A | * | 4/1994 | Myerholtz et al. | 436/149 |
| 5,436,161 | A | * | 7/1995 | Bergstrom et al. | 435/291 |
| 5,447,845 | A | * | 9/1995 | Chu et al. | 435/6 |
| 5,478,756 | A | * | 12/1995 | Gizeli et al. | 436/527 |
| 5,492,840 | A | * | 2/1996 | Malmqvist et al. | 436/518 |
| 5,554,541 | A | * | 9/1996 | Malmqvist et al. | 436/518 |
| 5,658,732 | A | * | 8/1997 | Ebersole et al. | 435/6 |
| 5,705,399 | A | * | 1/1998 | Larue | 436/501 |
| 5,753,518 | A | * | 5/1998 | Karlsson | 436/517 |
| 5,869,763 | A | * | 2/1999 | Vig et al. | 73/580 |
| 5,958,704 | A | * | 9/1999 | Starzi et al. | 435/7.1 |
| 5,972,612 | A | * | 10/1999 | Malmqvist et al. | 435/6 |
| 6,033,852 | A | * | 3/2000 | Andle et al. | 435/6 |
| 6,127,183 | A | * | 10/2000 | Ivarsson et al. | 436/34 |
| 6,134,944 | A | * | 10/2000 | Yu et al. | 73/23.35 |
| 6,143,574 | A | * | 11/2000 | Karlsson et al. | 436/517 |

FOREIGN PATENT DOCUMENTS

| | | | | | |
|---|---|---|---|---|---|
| EP | 0177191 | A1 * | 4/1982 | | G01N/33/537 |
| EP | 295 965 | B1 | 6/1994 | | |
| GB | 2084317 | A * | 4/1982 | | G01N/33/54 |
| WO | WO 89/09938 | | 10/1989 | | |
| WO | WO 90/11525 | | 10/1990 | | |
| WO | WO 91/05261 | | 4/1991 | | |
| WO | WO 95/24649 | | 9/1995 | | |
| WO | WO 95/27208 | | 10/1995 | | |
| WO | WO 96/06948 | | 3/1996 | | |
| WO | WO 97/04314 | | 2/1997 | | |
| WO | WO 98/26288 | | 6/1998 | | |

OTHER PUBLICATIONS

Janda et al., "Antibody Bait and Switch Catalysis: A Survey of Antigens Capable of Inducing Abzymes with Acyl–Transfer Properties," *J. Am. Chem. Soc. 113*(4):5427–5434, Jul. 31, 1991.

Jönsson et al., "Real–Time Biospecific Interaction Analysis Using Surface Plasmon Resonance and a Sensor Chip Technology," *Biotechniques 11*(5):620–627, Nov. 1991.

Karlsson et al., "Kinetic Analysis of Nomoclonal Antibody–antigen Interactions with a New Biosensor Based Analytical System," *J. Immunol. Methods 145*:229–240, 1991.

Mandenius et al., "Detection of Biospecific Interactions Using Amplified Ellipsometry," *Anal. Biochem. 170*(1):68–72, Apr. 1988.

* cited by examiner

*Primary Examiner*—Christopher L. Chin
*Assistant Examiner*—Pensee T. Do
(74) *Attorney, Agent, or Firm*—Seed Intellectual Property Law Group PLLC

(57) ABSTRACT

The invention relates to methods, kits and systems for determining an analyte in a liquid sample as well as the use thereof for concentration analysis and screening purposes. In one method, a specific binding partner to the analyte is permitted to compete with a conjugate containing the analyte or an analyte analogue for the binding to free analyte. The conjugate also contains a component that specifically binds to a solid support so that reacted and unreacted conjugate are bound thereto when the reaction solution is contacted with the solid support. The amount of analyte is then determined by measuring by a label-free mass-detection technique, such as surface plasmon resonance, the amount of binding partner immobilized on the solid support via the reacted conjugate. This is made possible by the binding partner having a considerably greater mass than the conjugate. Variants of this method are also disclosed.

23 Claims, 3 Drawing Sheets

METHOD AND SYSTEM FOR ANALYTE DETERMINATION

CROSS-REFERENCE TO RELATED APPLICATION

This application is a continuation of co-pending PCT Application No. SE97/02071, filed Dec. 11, 1997, which claims priority from Swedish Application Serial No. 9604575-2, filed Dec. 12, 1996, as provided for in 35 USC §120 and 35 USC §119(a) through (d), and in accordance with 35 USC §365.

FIELD OF THE INVENTION

The present invention relates to methods and systems, as well as assay kits, for the determination or screening of analytes in liquid samples, based on label-free determination of binding events at a solid phase surface.

BACKGROUND OF THE INVENTION

A wide variety of techniques for determining the concentration of a compound, usually referred to as analyte, in a liquid sample, are based on the binding of the analyte to a ligand immobilised on a solid support, below referred to as solid phase assays. Usually, the assays are of either sandwich or competitive type.

In a competitive type assay, analyte or an analyte analogue is allowed to compete with the analyte for the binding to the immobilised ligand, whereas in a sandwich type assay, a specific reagent is bound to the analyte, either before or after the analyte is bound to the immobilised ligand. While labelling with a marker is usually used to permit detection of the binding events, so-called label-free methods are also known, for example such based on surface plasmon resonance (SPR).

It has been desired in solid phase assays to provide a regeneratable surface of general character, i.e. a surface that easily permits the immobilized ligand to be removed and be replaced by binding a different ligand to the surface.

One type of such a surface is disclosed in U.S. Pat. No. 4,271,140, where a complex of the formula $A_{BL}(BL)_nA_1$ is adsorbed onto the surface. In the complex, BL is a binding ligand, n is at least 1, $A_{BL}$ is a receptor specific for BL, $A_1$ is a receptor for the analyte being assayed, BL is covalently bonded to $A_1$, and $A_{BL}$ is reversibly bonded to BL. Thus, a single surface coated with ligand binding receptor $A_{BL}$ may be used for different assays by reversibly binding and releasing different conjugates $(BL)_nA_1$ to the surface. This is a particular advantage in automated flow assay equipment. In a competitive specific binding assay, for example, based on this concept, the analyte and a labelled analyte analogue will compete for the binding to the immobilised conjugate $(BL)_nA_1$. A disadvantage of the above approach is, however, that in the conjugate $(BL)_nA_1$, the covalent binding of receptor $A_1$ to the binding ligand BL may have a negative influence on the receptor function.

The use of a universal support in a solid phase assay is also described in WO 95/24649. In this assay, one or more binding agents are provided with tail groups which can bind specifically to one or more capture agents immobilised on the support. The binding agent is usually an antibody, and the tail groups and the respective capture agents are complementary oligonucleotide sequences which can hybridise to each other. The assay is performed by sequentially or simultaneously contacting the sample with the binding agent (s) and the immobilised capture agent(s), and determining the fraction of binding sites of a binding agent occupied by the analyte to determine the concentration of the analyte in the sample.

A similar approach is described in WO 96/06948, where double stranded nucleic acid duplexes serve as universal cleavable link systems in different types of immunoassays. In an embodiment of competitive assay, one oligonucleotide is bound to the analyte or to an analogue thereof which is allowed to compete with the target analyte for a labelled immunoreagent. The second oligonucleotide is bound to a solid support. The analyte competitor will bind competitively with free analyte to the immunoreagent. When the reaction solution is contacted with the solid support under hybridising conditions, the oligonucleotide-coupled analyte or analyte analogue will bind to the support via an oligonucleotide duplex. By determining the concentration of label in the duplexes, the concentration of analyte may be determined.

A disadvantage common to all the above described methods is that they require some type of labelling.

Recently, label-free surface sensitive measuring techniques have been developed for measuring and quantifying biomolecular interactions. In these techniques, a receptor capable of binding to an analyte of interest is immobilised to a sensor surface, and binding of the analyte to the receptor is detected as a resulting change of a property of the sensor surface, such as a change in surface mass or surface refractive index. One type of such mass-sensing apparatus uses the phenomenon of surface plasmon resonance (SPR) to study the binding of analytes to receptors immobilized on the sensor surface. The apparatus and theoretical background are described in the literature (see e.g. Jönsson, U., et al., BioTechniques 11:620–627 (1991)).

However, for detecting a binding event at a mass detecting sensor surface, the species binding to the surface must be rather large, i.e have a relatively high molecular weight, as the binding of a small molecule to the surface will usually not give a sufficient mass change to be detectable. Prior art assay formats based on the use of a label are therefore in general not readily transformable to a label-free assay format based on mass detection at a sensor surface.

The object of the present invention is therefore to provide novel assay methods and systems which use a regeneratable, or rechargeable, solid support surface of universal character, and which are based on surface mass-sensing and therefore label-free.

SUMMARY OF THE INVENTION

Accordingly, in a first aspect, the present invention provides a method of determining an analyte in a liquid sample, comprising the steps of:

a) providing a solid support having immobilized thereto one member of a specific binding pair capable of reversibly binding to the other member of the specific binding pair, b) providing a conjugate comprising (i) the analyte, or an analyte competitor, and (ii) the other member of said specific binding pair, c) simultaneously or sequentially contacting a liquid sample containing or suspected of containing the analyte (with a specific binding partner to the analyte) and with said conjugate, said binding partner having a molecular weight of at least five times that of said conjugate, d) contacting the reacted liquid sample with the solid support to bind reacted and unreacted conjugate to the solid support, e) determining by mass-sensing at the solid support the amount of analyte binding partner that has bound in step d) to the solid support via said conjugate to determine therefrom analyte in the sample, and f) regenerating the solid support by subjecting the surface thereof to conditions which disrupt the binding between the members of said specific binding pair to release the conjugate from the solid support and prepare the surface for a subsequent determination.

In a second aspect, the present invention provides a method of determining an analyte in a liquid sample, comprising the steps of:

a) providing a solid support having immobilized thereto one member of a specific binding pair capable of reversibly binding to the other member of the specific binding pair, b) providing a conjugate between (i) the analyte, or an analyte competitor, and (ii) the other member of said specific binding pair, c) contacting said conjugate with said solid support to bind conjugate thereto, d) contacting a liquid sample containing or suspected of containing the analyte with a specific binding partner to the analyte, said binding partner having a molecular weight of at least five times that of said conjugate, e) contacting the reacted liquid sample with the solid support having said conjugate immobilised thereto to bind unreacted analyte binding partner thereto, f) determining by mass-sensing at the solid support the amount of analyte binding partner that has bound in step e) to the solid support via said conjugate to determine therefrom analyte in the sample, and g) regenerating the solid support by subjecting the surface thereof to conditions which disrupt the binding between the members of said specific binding pair to release the conjugate from the solid support and prepare the surface for a subsequent determination.

In a third aspect, the present invention provides a method of determining an analyte in a liquid sample, comprising the steps of:

a) providing a solid support having immobilized thereto one member of a specific binding pair capable of reversibly binding to the other member of the specific binding pair, b) providing a conjugate between (i) the analyte, or an analyte competitor, and (ii) the other member of said specific binding pair, c) simultaneously or sequentially contacting a liquid sample containing or suspected of containing the analyte with a specific binding partner to the analyte and with the conjugate, d) contacting the reacted liquid sample with the solid support to bind reacted and unreacted conjugate to the solid support, e) contacting the solid support with a reagent which specifically binds to said binding partner, said reagent having a molecular weight of at least five times that of a complex between binding partner and conjugate, f) determining by mass-sensing at the solid support the amount of said reagent that has bound in step d) to analyte binding partner bound to the solid support via said conjugate to determine therefrom analyte in the sample, and g) regenerating the solid support by subjecting the surface thereof to conditions which disrupt the binding between the members of said specific binding pair to release the conjugate from the solid support and prepare the surface for a subsequent determination.

In a fourth aspect, the present invention provides a method of determining an analyte in a liquid sample, comprising the steps of:

a) providing a solid support having immobolized thereto one member of a specific binding pair capable of reversibly binding to the other member of the specific binding pair, b) providing a conjugate between (i) the analyte, or an analyte competitor, and (ii) the other member of said specific binding pair, c) contacting said conjugate, with said solid support to bind conjugate thereto, d) contacting a liquid sample containing or suspected of containing the analyte with a specific binding partner to the analyte, e) contacting the reacted liquid sample with the solid support to bind unreacted binding partner to conjugate immobilised on the solid support, f) contacting the solid support with a reagent which specifically binds to said binding partner, said reagent having a molecular weight of at least five times that of a complex of binding partner and conjugate, g) determining by mass-sensing at the solid support the amount of said reagent that has bound in step f) to analyte binding partner bound to the solid support via said conjugate to determine therefrom analyte in the sample, and h) regenerating the solid support by subjecting the surface thereof to conditions which disrupt the binding between the members of said specific binding pair to release the conjugate from the solid support and prepare the surface for a subsequent determination.

In a fifth aspect, the present invention provides a method of determining an analyte in a liquid sample, comprising the steps of:

a) providing a solid support having immobilized thereto one member of a first specific binding pair capable of reversibly binding to the other member of said first specific binding pair, b) providing a conjugate comprising (i) the analyte, or an analyte competitor, (ii) the other member of said first specific binding pair, and (iii) one member of a second specific binding pair, c) simultaneously or sequentially contacting a liquid sample containing or suspected of containing the analyte with a specific binding partner to the analyte and with said conjugate, d) contacting the reacted liquid sample with the solid support to bind unreacted conjugate to the solid support, complex formation between conjugate and specific binding partner preventing conjugate from binding to the support, e) contacting the solid support with the other member of said second specific binding pair to permit said other member to bind to the conjugate, said other member having a molecular weight of at least five times that of said conjugate, f) determining by mass-sensing at the solid support the amount of said other member that has bound in step e) to said conjugate bound to the solid support to determine therefrom analyte in the sample, and g) regenerating the solid support by subjecting the surface thereof to conditions which disrupt the binding between the members of said first specific binding pair to release the conjugate from the solid support and prepare the surface for a subsequent determination.

In a sixth aspect, the present invention provides a method of determining an analyte in a liquid sample, comprising the steps of:

a) providing a solid support having immobilized thereto one member of a first specific binding pair capable of reversibly binding to the other member of said first specific binding pair, b) providing a conjugate comprising (i) the analyte, or an analyte competitor, (ii) the other member of said first specific binding pair, and (iii) a carrier having a molecular weight of at least 5,000 daltons, c) simultaneously or sequentially contacting a liquid sample containing or suspected of containing the analyte with a specific binding partner to the analyte and with said conjugate, d) contacting the reacted liquid sample with the solid support to bind unreacted conjugate to the solid support, complex formation between conjugate and specific binding partner preventing conjugate from binding to the support, e) determining by mass-sensing at the solid support the amount of said conjugate that has bound in step d) to the solid support to determine therefrom analyte in the sample, and f) regenerating the solid support by subjecting the surface thereof to conditions which disrupt the binding between the members of said first specific binding pair to release the conjugate from the solid support and prepare the surface for a subsequent determination.

In a seventh aspect, the present invention provides an assay kit for an analyte, comprising:

a) a solid support having immobilized thereto one member of a specific binding pair capable of reversibly binding to the other member of the specific binding pair, b) a specific binding partner to the analyte, which binding partner is unlabelled, c) a conjugate between (i) the analyte, or an analyte analogue, and (ii) the other member of said specific binding pair, which conjugate binds competitively with free analyte to said binding partner, said specific binding partner in b) having a molecular weight of at least five times that of the conjugate.

In an eighth aspect, the present invention provides an assay kit for an analyte, comprising:

a) a solid support having immobilized thereto one member of a specific binding pair capable of reversibly binding to the other member of the specific binding pair, b) a specific binding partner to the analyte, which binding partner is unlabelled, c) a conjugate comprising (i) the analyte, or an analyte analogue, and (ii) the other member of said specific binding pair, which conjugate binds competitively with free analyte to said binding partner, and d) a reagent which binds specifically to said binding partner, which reagent is unlabelled, said reagent in d) having a molecular weight of at least five times that of a complex between conjugate and binding partner.

In a ninth aspect, the present invention provides an assay kit for an analyte, comprising:

a) a solid support having immobilized thereto one member of a first specific binding pair capable of reversibly binding to the other member of said first specific binding pair, b) optionally, a specific binding partner to the analyte, which binding partner is unlabelled, c) a conjugate comprising (i) the analyte, or an analyte analogue, (ii) the other member of said first specific binding pair, and (iii) one member of a second specific binding pair, which conjugate binds competitively with unconjugated analyte to said binding partner, and d) the other member of said second specific binding pair, which member is unlabelled, said other member in d) having a molecular weight of at least five times that of the conjugate.

In a tenth aspect, the present invention provides an assay kit for an analyte, comprising:

a) a solid support having immobilized thereto one member of a specific binding pair capable of reversibly binding to the other member of said specific binding pair, b) optionally, a specific binding partner to the analyte, which binding partner is unlabelled, and c) a conjugate comprising (i) the analyte, or an analyte analogue, (ii) the other member of said specific binding pair, and (iii) a carrier molecule having a molecular weight of at least 5,000 daltons, which conjugate binds competitively with unconjugated analyte to said binding partner.

In an eleventh aspect, the present invention provides an assay kit for an analyte, corresponding to any one of the assay kits defined above but wherein the conjugate is replaced by a pre-conjugate lacking the analyte or analyte analogue part of the conjugate.

In a twelfth aspect, the present invention provides an assay system for an analyte, which comprises, in addition to any of the assay kits described above, an apparatus for detection by mass-sensing of binding events at the solid support.

In a thirteenth aspect, the present invention provides the use of any one of the method and system aspects described above for concentration analysis, preferably of small molecules, and for drug screening.

DETAILED DESCRIPTION OF THE INVENTION

Figure 1:
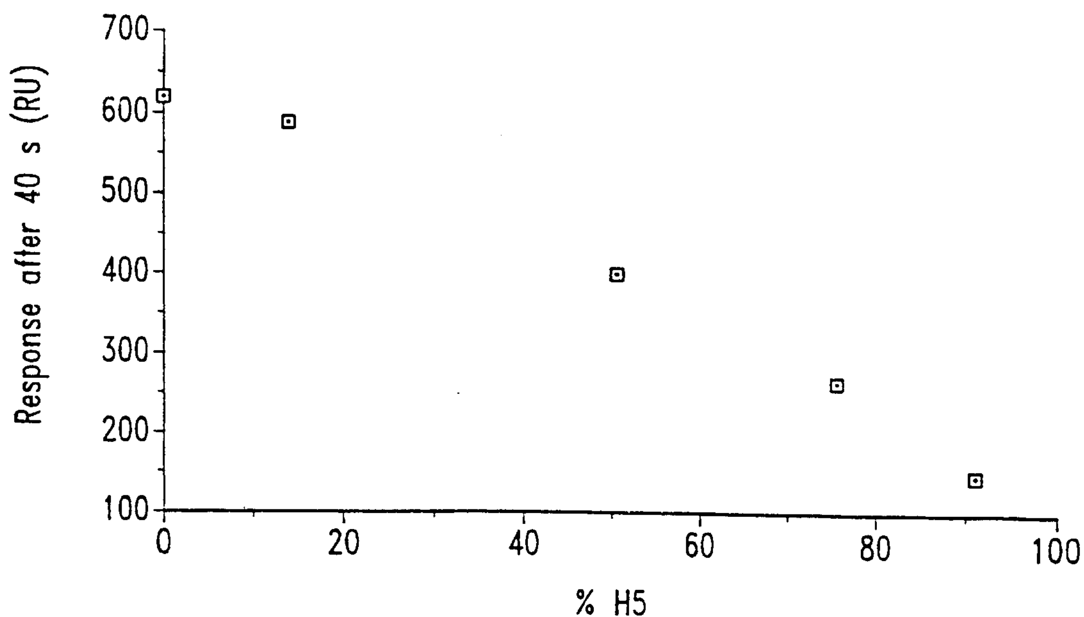
FIG. 1 is an inhibition curve for SPR response versus concentration of hapten H5 obtained in a method embodiment of the invention.

As mentioned above, the invention is directed to a method and a system for assaying for analytes in liquid samples, utilising a surface mass-sensing technique.

Such mass detecting techniques are well-known in the art and include piezoelectric, optical, thermo-optical, surface acoustic wave (SAW) methods, as well as electrochemical methods, such as potentiometric, voltametric, conductometric, amperometric and capacitance methods.

Among optical methods may particularly be mentioned those that detect mass surface concentration (or refractive index), such as reflection-optical methods, including both internal and external reflection methods, e.g. ellipsometry and evanescent wave spectroscopy (EWS), the latter including surface plasmon resonance spectroscopy (SPRS), Brewster angle refractometry, critical angle refractometry, frustrated total reflection (FTR), evanescent wave ellipsometry, scattered total internal reflection (STIR), optical wave guide sensors, evanescent wave based imaging, such as critical angle resolved imaging, Brewster angle resolved imaging, SPR angle resolved imaging, etc., as well as methods based on evanescent fluorescence (TIRF) and phosphorescence. Additionally, optical methods based on interference as well as on methods based on surface enhanced Raman spectroscopy and surface enhanced resonance Raman spectroscopy may be mentioned.

Analytical apparatus based on surface mass sensing are also commercially available. One type of such apparatus (with associated computer control and data-processing means) include the commercial instrument BIACORE® (BIACORE is a trademark of Biacore AB, Uppsala, Sweden; wherein BIA stands for biospecific interaction analysis) which uses the phenomenon of surface plasmon resonance (SPR) to study the binding of analytes to receptors immobilized on a sensor chip. The apparatus and theoretical background are fully described in the literature (see e.g. J önsson, U., et al., BioTechniques 11:620–627 (1991)). Essentially, the technique involves the immobilisation of a receptor to the special surface of a sensor chip, contacting the sensor chip with a flow of sample containing the analyte of interest, and then measuring the change in the surface optical characteristics of the sensor chip arising form the binding of interest.

A related such commercial instrument based on FTR instead of SPR is marketed under the trade name IASYS by Affinity Systems Ltd, U.K.

For detecting a binding event at a mass detecting sensor surface, the species binding to the surface must be rather large, i.e. have a rather high molecular weight. In other words, the binding of a small molecule to the surface can usually not be seen directly. Prior art assay formats based on the use of a label are therefore not readily transformable to a label-free assay format based on mass detection at a sensor surface.

The present invention provides a competitive assay method and system, respectively, which use surface mass detection at a regeneratable sensor surface. Regeneratable in this context means that the ligand or binding species immobilised on the surface may conveniently be released and replaced by the same or a different ligand or binding species.

A salient feature of the invention is the use of a conjugate which competes with the analyte for the binding to a specific binding partner for the analyte. This conjugate contains (i) a varying part which includes the analyte, or analyte analogue, and (ii) a constant, or common, part which is one member of a specific binding pair. (The term analogue herein means a competitor molecule capable of specifically binding to the binding partner in the same way as the analyte). The other member of this binding pair is bound to the sensor surface. Thus, whereas the conjugates may have varying analyte or analyte analogue parts depending on the analytes to be assayed for, the binding pair member part thereof is always identical. The sensor surface that supports the other member of the binding pair may therefore be of a common, or universal, nature and may be used for a number of different conjugates.

In the conjugate, the analyte or analyte analogue may be bound directly to the binding pair member or via a chemical structure, such as a coupling sequence or linker. To design and prepare a suitable conjugate for any particular situation is readily within the competence of the skilled person and need not be described in any detail herein.

The binding partner and the analyte may be said to form a ligand-receptor pair together with the analyte. While, as a general rule, the receptor is the larger of the two components of the pair, receptors may also include low molecular weight substances. For the purposes of the present invention, the receptor is to be construed as simply one component of a binding pair with the analyte, in which the receptor may be larger or smaller than the analyte.

Usually, however, the binding partner is a macromolecule, typically an immunoreactant, such as an antibody or an immunoreactive fragment thereof.

The analyte, on the other hand, is typically a small molecule, which can not be determined directly by conventional mass-sensing methods. Exemplary analytes are vitamins, drugs, pathogens, steroids, hormones, pesticides and toxins, such as bacterial toxins.

The above-mentioned specific binding pair, one member of which is part of the conjugate and the other member of which is immobilized on the sensor surface, should be reversible, i.e. the binding should be disruptible without affecting the surface-bound member to permit the sensor surface to be regenerated, or recharged, in the sense that the surface-bound member is prepared for renewed binding of the other member of the binding pair. Exemplary such specific binding pairs are antigen-antibody, antibody-hapten, oligonucleotide-oligonucleotide, hormone-hormone receptor, protein A or G-immunoglobulin, lectin-carbohydrate. Other suitable binding-pairs will be obvious to the skilled person.

With respect to the terms antibodies and haptens used herein, antibodies are immunoglobulin molecules (serum proteins) of which there are several classes. Each class has its own characteristic molecular size, electrophoretic migration velocity, carbohydrate content, etc. Antibodies can be broken into fragments, such as the Fab fragment and the Fc fragment. The Fab fragment, like intact antibodies, can bind antigenic substances, e.g. antigens and haptens. The term antibody is intended to include also active antibody fragments as well as recombinantly produced antibodies and active fragments thereof.

An antigen is any substance that will provoke an immune response. In general, antigens are considered greater than 10,000 in molecular weight and are proteins, carbohydrates or glycoproteins. Smaller, less rigid molecules are not normally antigenic in pure form, but can be made so by linking them to larger molecules. These smaller molecules are called haptens.

In one method embodiment, a sample that contains or is suspected of containing the analyte is contacted, either simultaneously or in sequence, with the conjugate and a specific binding partner to the analyte. The conjugate will then compete with the analyte for the binding to the analyte binding partner. The reaction solution is then brought to contact the sensor surface to bind conjugate thereto. Both unreacted conjugate and conjugate-analyte binding partner complexes that have formed will bind to the surface via the specific binding pair.

The amount of binding partner bound to the surface via the conjugate is then determined by sensing the mass change at the surface. This amount is inversely correlated to the concentration of analyte in the sample, i.e. the more analyte in the sample, the less binding partner is bound to the surface.

The amount of surface-bound complex between binding partner and conjugate may be determined by either (i) sensing the surface mass change caused by the binding of the binding partner/conjugate complex to the surface, or (ii) contacting the binding partner/conjugate complex on the sensor surface with a specific binding reagent to the binding partner and sensing the surface mass change caused by the binding of this reagent to the binding partner/conjugate complex on the sensor surface.

In the first case (i), for the mass change to be detectable by conventional mass-sensing methods, such as those mentioned above, the binding partner should have a mass that is at least five times, preferably at least 10 times, and more preferably at least 25 times that of the conjugate. In practice, the binding partner would in most cases have a molecular weight of at least 5000 daltons, and usually at least 10000 daltons. A typical molecular weight of the conjugate, on the other hand, is in the range of 500 to 1500 daltons.

In the second case (ii), for the mass change to be detectable at the sensor surface, the specific reagent to the binding partner should have a mass that is at least five times, preferably at least 10 times, and more preferably at least 25 times that of the binding partner/conjugate complex.

After the mass-sensing procedure at the sensor surface is completed, the surface is regenerated by subjecting the surface to conditions that break or disrupt the bond between the conjugate and the binding pair member immobilized on the sensor surface without affecting the binding activity of the immobilized binding pair member. Suitable conditions for regeneration depend i.a. on the particular conjugate and its binding to the surface and are well-known to the skilled person. The sensor surface is then ready for use in a new assay for the same or a different analyte.

In a variant of the above embodiment, the conjugate is first bound to the sensor surface, via the specific binding pair member, and the sensor surface is then contacted with the liquid sample and the binding partner to the analyte.

A kit for carrying out the above method embodiment may comprise a solid support, such as a sensor chip, with a conjugate-binding agent immobilized thereto, a conjugate between (i) the analyte or analyte analogue and (ii) a component capable of binding to the conjugate-binding on the solid support, and a specific binding partner to the analyte and the analyte analogue.

In another method embodiment of the invention, the above described conjugate is modified to the extent that it in addition to the analyte, or analyte analogue, and specific binding pair components also has a third component in the form of one member of a second specific binding pair, which may be of the same type as that of the first specific binding pair described above. The other member of this second binding pair is used for identifying conjugate bound to the sensor surface. A characteristic feature of this embodiment is that analyte binding partner conjugate complex formed is prevented from binding to the sensor surface. This method embodiment is carried out as follows.

The sample is contacted with the analyte binding partner and with the conjugate, either simultaneously or sequentially. The analyte in the ample will then compete with the conjugate for the binding to the binding partner. Then the reaction solution is contacted with a sensor surface having the other member of the first binding pair immobilized on the surface. As mentioned above, and as will be described in more detail below, reacted conjugate, i.e. analyte binding partner conjugate complex formed, is unable to either reach the sensor surface or to bind thereto. Thereby, only unreacted conjugate will bind to the sensor surface. The other member of the second binding pair or "secondary reagent", e.g. an antibody, is then added to determine the binding of the conjugate to the surface by mass-sensing.

For the mass change to be detectable at the sensor surface, the above-mentioned other member of the second binding pairs should have a mass that is at least five times, preferably at least 10 times, and more preferably at least 25 times that of the conjugate.

The amount of binding of the second binding pair member to the sensor-bound conjugate is positively correlated to the concentration of analyte in the sample, i.e. the more analyte in the sample, the more conjugate is bound to the surface, and the more secondary reagent is bound to the immobilized conjugate.

After the mass-sensing procedure at the sensor surface is completed, the surface is regenerated as described above by subjecting the surface to conditions that break or disrupt the bond between the conjugate and the binding pair member immobilized on the sensor surface.

As mentioned above, the analyte binding partner conjugate complex formed in the assay is prevented from binding to the sensor surface. This may be accomplished in several ways. For example, the binding partner may be supported on a particulate carrier that is substantially not soluble in the sample and is typically a cell receptor. If the assay is performed in a flow cell or the like where the sample is made to pass over the sensor surface in a liquid flow, the flow conditions may be selected such that particles of the size of a cell will not be prone to diffuse to the walls of the flow cell but will remain collected in the core of the liquid stream. This phenomenon is generally known as the F ȧhreus-Lindqvist effect and is attained at a laminar flow of high rate. The use of this effect in a biosensor flow cell is described in WO 95/27208, to which it is referred for further details.

The non-soluble particulate matter may, of course, also be prevented from reaching the surface by other means, such as subjecting the reaction solution to a separation procedure prior to contacting the solution with the sensor surface. In still another alternative, the binding partner may be bound to a support surface which is contacted with the analyte-containing sample and the conjugate before the reaction solution is contacted with the sensor surface to bind unreacted conjugate thereto.

In case the analyte binding partner is water soluble, such as a soluble cell receptor, reacted conjugate may be prevented from binding to the sensor surface by designing the conjugate such that binding of the conjugate to the receptor sterically blocks or hinders its binding to the immobilized binding pair member on the sensor surface. The conjugate may, for example, include a hapten for binding to a corresponding antibody on the sensor surface and analyte or analyte analogue located very near each other.

It is readily seen that the above described method embodiment may be used for screening or characterizing the binding of low molecular weight compounds (analytes) to cell-bound and soluble receptors. In other words, the method may not only be used for measuring the concentration of an analyte in a sample, but also for screening purposes, such as drug screening, where the analyte is a set of molecules, e.g. drug candidates, which it is desired to screen for their binding to e.g. a cell receptor. One general conjugate can thus be used for analysis of various low molecular weight compounds. This in turn makes it possible to design a special reagent which is optimized in respect of binding to the sensor surface and regeneration conditions.

A kit for carrying out the above method may comprise a solid support, such as a sensor chip, with a conjugate-binding agent immobilized thereto, a conjugate as specified above, and a secondary reagent capable of binding to the conjugate.

In a variation of the above described embodiment, the binding of free conjugate in the reaction solution conjugate is measured directly at the sensor surface rather than using a secondary reagent to verify the surface-binding thereof. That is, the conjugate itself must have a sufficient mass for its binding to the surface to create a mass change detectable by mass-sensing, practically of at least 5,000 daltons, and preferably at least 10,000 daltons, whereby the binding partner for the secondary reagent on the conjugate, of course, will not be necessary. Such a conjugate may be produced by conjugating the analyte or analogue and the surface-binding molecule to a macromolecule of some kind. The latter may e.g. be a protein or other biomolecule but may also be another type of polymer, e.g. a starburst dendrimer molecule, which is a polymer with a specific molecular weight and with suitable selected properties in terms of hydrophilicity and coupling groups. Optionally, one may first make a conjugate between the analyte or analyte analogue and the surface-binding molecule, and then bind this conjugate to the macromolecular carrier. Alternatively, a conjugate having a third binding component may be prepared and then coupled by (preferably non-covalent binding) to a macromolecule capable of binding thereto. Still another alternative is to introduce an epitope in a fusion protein together with a coupling site, for example a cysteine residue, for linkage of the analyte or analyte analogue.

A kit for carrying out the above method variant may comprise a solid support, such as a sensor chip, with a conjugate-binding agent immobilized thereto, and a modified conjugate as specified above.

In all the above mentioned kit variants, the conjugate may optionally be replaced by a pre-conjugate in the form of the "common" part or parts thereof, i.e. the surface binding component and, when present, the component binding to secondary reagent, so that the customer may prepare the conjugate himself by binding a desired varying part, i.e. the analyte or analyte analogue, thereto.

The various method embodiments described above may readily be optimized by the skilled person. Thus, suitable amounts of and proportions between conjugate and analyte binding partner as well as concentrations of immobilized conjugate capture agent on the sensor surface is readily determined by the skilled person in each specific case to obtain optimum sensitivity and accuracy.

In the following, the invention is illustrated by some non-limiting Examples.

Measurements were performed with a BIACORE® analytical instrument (Biacore AB, Uppsala, Sweden). The instrument measures binding between two (or more) molecules in a hydrophilic gel matrix of about 100 nm thickness. One molecule (ligand) is covalently coupled to a carboxymethyldextran-modified gold surface, which allows a restricted diffusion of the ligand. This surface forms one side of a flow chamber, through which a solution of the other molecule (analyte) is flowing. The refractive index change resulting from analyte bound to the ligand in this surface layer is monitored by surface plasmon resonance (Karlsson, R., et al., J. Immunol. Methods 145:229–240 (1991)). The sensitivity of this method is limited by noise at a resonance signal at about 1 RU (resonance unit) which is equivalent to $10^{-9}$ kg/m$^2$.

EXAMPLE 1

Measurement of H5 Hapten

Preparation of H5-aminotheophylline Conjugate

To a solution of 12.3 mg (40 $\mu$mol) of aminotheophylline in 1.0 ml DMF were added under nitrogen 6.2 mg (73.8 $\mu$mol) of $NaHCO_3$ and 9.0 mg (20.5 $\mu$mol) of hapten H5a (4-[[5-[(2,5-dioxo-1-pyrrolidinyl)oxy]-1,5-dioxopentyl]amino]-N,N-dimethyl-N-phenylbenzene-methanaminium bromide, molecular weight 422 daltons, synthesized according to Janda et al., J. Am. Chem. Soc., 113, 5427–5434 (1991)). The mixture was stirred under nitrogen for 3 hours. The reaction mixture was then evaporated and purified by flash chromatography.

Immobilization of Anti-aminotheophylline Antibody

Anti-aminotheophylline IgG-antibody 451 (Biacore AB, Uppsala, Sweden) (Mw about 150,000) was immobilized to a sensor chip CM5 (Biacore AB) with EDC, NHS and ethanolamine according to the manufacturer's instructions by injecting 30 $\mu$l of anti-aminotheophylline antibody diluted to 67 $\mu$g/ml in 10 mM acetic acid, pH 4.5. A response of about 9500 RU was obtained in the immobilization.

Inhibition Studies

To 2:1 mixtures of H5-aminotheophylline conjugate and anti-H5 IgG-antibody (Mw about 150,000, Biacore AB) were added different concentrations of free H5 hapten, and 35 $\mu$l samples diluted in drive buffer (HBS) were injected over the CM5 surface. From the sensorgrams obtained, the concentration of free H5 in each sample was calculated. A representative inhibition curve obtained is shown in FIG. 1.

Regeneration of Sensor Chip Surface

Regeneration of the CM5 surface between the injections was performed by 5 $\mu$l regeneration pulses of 10 mM NaOH at pH 10.85.

EXAMPLE 2

Measurement of Theophylline

Preparation of H5-aminotheophylline Conjugate

H5-aminotheophylline conjugate was prepared as in Example 1 above.

Immobilization of Anti-H5 Antibody

Anti-H5 IgG-antibody was immobilized to a sensor chip CM5 (Biacore AB) with EDC, NHS and ethanolamine according to the manufacturer's instructions by injecting 30 $\mu$l of anti-H5 antibody diluted to 40 $\mu$g/ml in 10 mM acetic acid, pH 5.05. A response of about 10,900 RU was obtained in the immobilization.

Inhibition Studies

Figure 2:
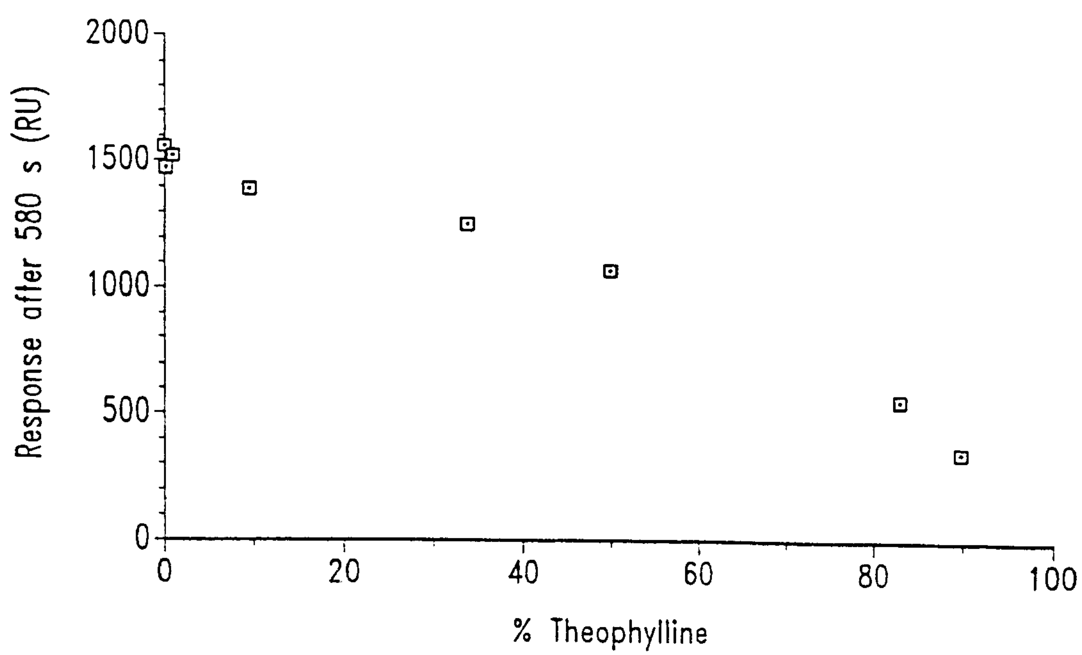
FIG. 2 is an inhibition curve for SPR response versus concentration of theophylline obtained in a method embodiment of the invention.

To 10:9 mixtures of H5-aminotheophylline conjugate (133.3 nM) and anti-aminotheophylline antibody (Mw about 150,000, Biacore AB) (121.3 nM) were added different concentrations of free theophylline, and 35 $\mu$l samples diluted in drive buffer (HBS) were injected over the CM5 surface. From the sensorgrams obtained, the concentration of free theophylline in each sample was calculated. A representative inhibition curve obtained is shown in FIG. 2.

Regeneration of Sensor Chip Surface

Regeneration of the CM5 surface between the injections was performed by 5 $\mu$l regeneration pulses of 10 mM glycine adjusted to pH 2.2 with 1 M HCl.

EXAMPLE 3

Measurement of FITC

Immobilization of Biotinylated Oligonucleotide

A 17 bp biotinylated oligonucleotide of the sequence 5'-biotin-AAGACACTCTTTCTCCC was prepared and immobilized to a streptavidin-coated sensor chip, Sensor Chip SA (Biacore AB, Uppsala, Sweden) according to the manufacturer's instructions.

Inhibition Studies

Figure 3:
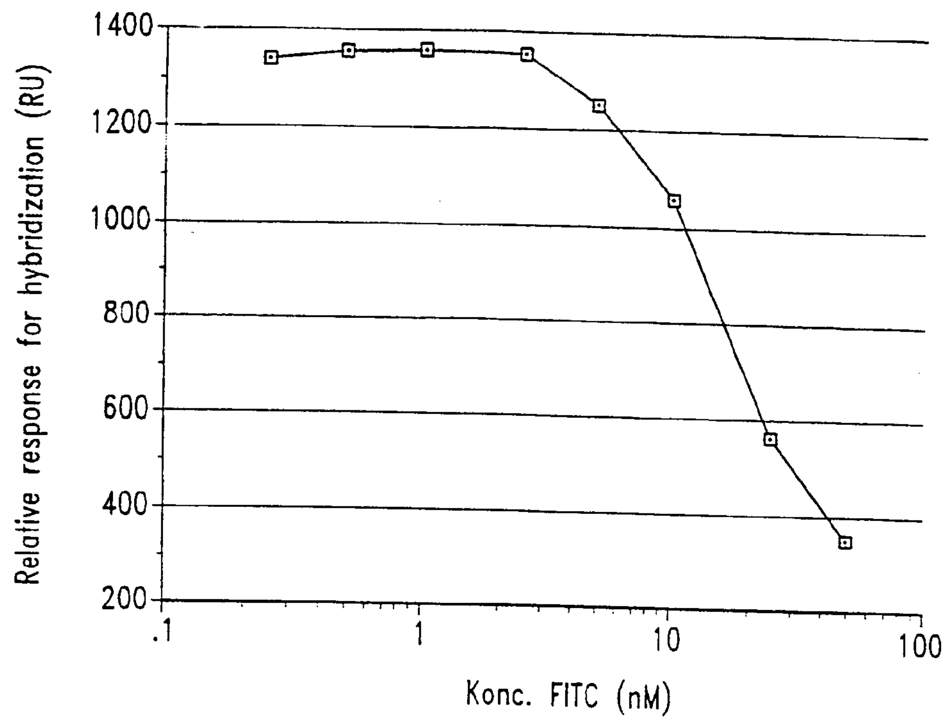
FIG. 3 is an inhibition curve for SPR response versus concentration of FITC obtained in a method embodiment of the invention.
Figure 4:
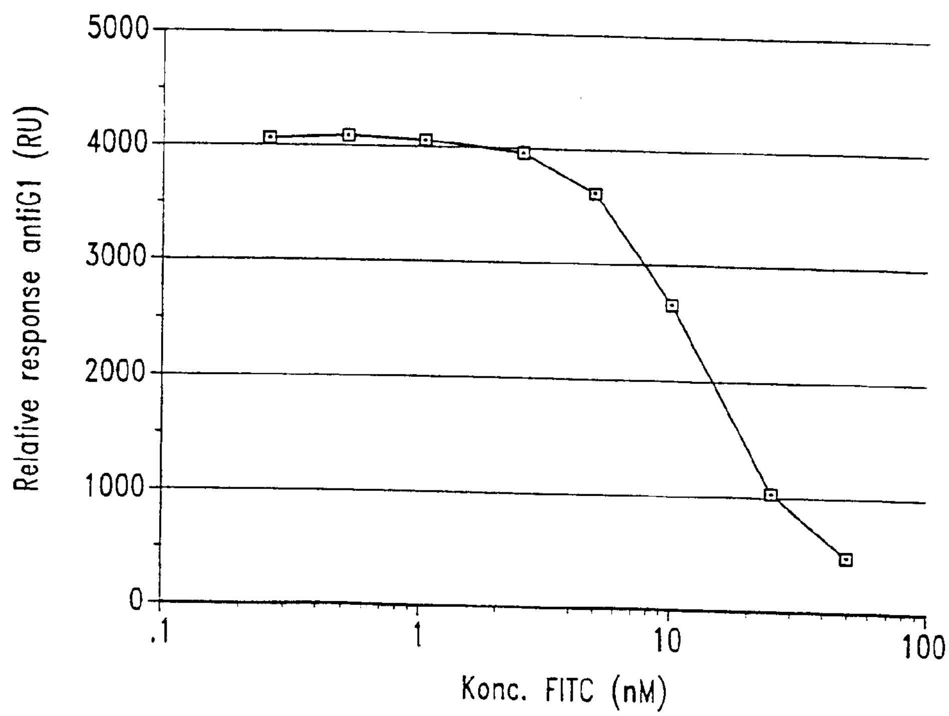
FIG. 4 is an inhibition curve for SPR response versus concentration of FITC obtained as in FIG. 3 except that a secondary reagent was used for determining the surface response.

FITC (fluorescein isothiocyanate) in the concentration range 0.1–50 nM was mixed with 10 nM of a FITC-labelled oligonucleotide of the sequence TTCTGTGAGAAAGAGGG-5', complementary to the immobilized oligonucleotide above. Monoclonal anti-FITC antibody was then added to a concentration of 1 μg/ml. The solutions were incubated at room temperature for 30 minutes and were then injected into the BIACORE® instrument over the SA sensor chip surface prepared above. The response was increased by injecting RAMG1 antibody (as a secondary reagent). From the sensorgrams obtained, the concentration of free FITC in each sample was calculated and plotted against the response. Two inhibition curves were obtained, one based on direct measurement of the hybridization response at the sensor surface, FIG. 3, and the other based on measurement of the enhanced response obtained through RAMG1 binding, FIG. 4. As shown in FIGS. 3 and 4, the response enhancement by secondary reagent addition (RAMG1) is not necessary in this particular case.

Regeneration of Sensor Chip Surface

The oligonucleotide-modified SA surface was regenerated between the analysis cycles with 100 nM NaOH.

EXAMPLE 4

Use of a PEG-conjugate in a Model for Competitive Cell Based Assay

Preparation of Polyetyleneglycol-LC-biotin-jeffamine-H1 (m-PEG-LC-biotin-JA-H1) Conjugate N-H1-N'-BOC-3,6-dioxaoctane-1,8-diamine (H1jeffamine-BOC)

26 μl (150 μmol) of N,N-diisopropylethylamine was added to a stirred solution of 30.9 mg (100 μmol) of the hapten H1 (N-methyl-N-p-nitrobenzyl-5-aminopentanoic acid) in 0.3 ml of DMF, 0.3 ml of dioxane and 0.3 ml of deionized water, followed by 33.2 mg (110 μmol) of TSTU (O-(N-Succinimidyl)-N,N,N',N'-tetramethyluronium tetrafluoroborate). The mixture was stirred at room temperature for 25 minutes, then 32.3 mg (130 μmol) of N-BOC-3,6-dioxaoctane-1,8-diamine was added. The mixture was stirred for additional 110 minutes, then 5.6 mg (12.6 μmol) of TSTU was added. The mixture was stirred for additional 35 minutes, then 3.8 mg (18.6 μmol) of TSTU was added. The mixture was stirred over night. The dioxane and water was removed in vacuo and the residue was dissolved in 4 ml of 1:40 ammonia/methanol. Purification by MPLC (column length 100 mm, I.D. 15 mm, flow 15 ml/min) using 40, 50 and 100 ml of 1:40, 1:20, 1:10 ammonia/methanol as the eluent gave 60.3 mg of the product as a yellow solid. TLC $R_f$ 0.40 (1:10 ammonia/methanol).

N-H1-3,6-dioxaoctane-1,8-diamine (H1-jeffamine or JA-H1)

1.0 ml of 5.6 M hydrochloric acid in 2-propanol was added to a stirred solution of 60.3 mg (≦100 μmol) of N-H1-N'-BOC-3,6-dioxaoctane-1,8-diamine in 5.0 ml of 2-propanol. The mixture was stirred for 110 minutes at room temperature. The solvent was removed in vacuo and the residue was dissolved in 2.5 ml of 8:2 methylene chloride/methanol. Purification by MPLC (column length 75 mm, I.D. 15 mm, flow 15 ml/min) using 110 ml of 8:2 methylene chloride/methanol followed by 110 ml of 32:7:1 methylene chloride/methanol/ammonia as the eluent gave 26.7 mg of the product as a white solid. TLC $R_f$ 0.54 (32:7:1 methylene chloride/methanol/ammonia).

$N^{\alpha}$-(tert-butyloxycarbonyl)-$N^{\beta}$-(LC-biotin)-L-diaminopropionic acid (BOC-DAP-LC-biotin)

30.0 mg (66 μmol) of NHS-LC-biotin was added to a stirred solution of 13.5 mg (66 μmol) of $N^{\alpha}$-(tert-butyloxycarbonyl)-L-diaminopropionic acid in 1.0 ml DMF and 0.6 ml deionized water. The mixture was stirred at room temperature for 6 hours. The solvent was removed in vacuo and the residue was dissolved in 2.5 ml of 80:17.5:2.5 methylene chloride/methanol/ammonia. Purification by MPLC (column length 85 mm, I.D. 15 mm, flow 15 ml/min) using 50, 100 and 50 ml of 80:17.5:2.5, 70:25:7:4.3, 70:35:5 methylene chloride/methanol/ammonia as the eluent gave 25.6 mg of the product as a white solid. TLC $R_f$ 0.28 (70:25.7:4.3 methylene chloride/methanol/ammonia).

BOC-DAP-LC-biotin-JA-H1

2.0 mg (20 μmol) of triethyl amine was added to a stirred solution of 5.44 mg (10 μmol) of BOC-DAP-LC-biotin in 1.09 ml DMF followed by 1.5 mg (11 μmol) of isobutyl chloroformate. The mixture was stirred at room temperature for 20 minutes, then 4.75 mg (11 μmol) of JA-H1 dissolved in 0.95 ml of methanol was added. The mixture was stirred for additional 20 minutes. The solvent was removed in vacuo and the residue was dissolved in 2.0 ml of 9:1 methylene chloride/methanol. Purification by MPLC (column length 90 mm, I.D. 15 mm, flow 15 ml/min) using 40,100 and 50 ml of 9:1, 8:2, 7:3 methylene chloride/methanol as the eluent gave 7.9 mg of the product as an off-white solid. TLC $R_f$ 0.52 (7:3 methylene chloride/methanol).

DAP-LC-biotin-JA-H1

A mixture of 7.9 mg (8.2 μmol) of BOC-DAP-LC-biotin-JA-H1, 2.0 ml 5.6 M hydrochloric acid in 2-propanol and 2.0 ml of methanol was stirred overnight. The solvent was removed in vacuo to yield 7.9 mg TLC $R_f$ 0.07 (7:3 methylene chloride/methanol).

m-PEG-LC-biotin-JA-H1

17.4 mg (3.4 μmol) of m-PEG succinimidyl carbonate (Mw 5,000 dalton) and 0.5 ml of 0.1 M $NaHPO_4$, pH 7.5, was added to a stirred solution of 1.5 mg (1.2 μmol) of DAP-LC-biotin-JA-H1 in 0.2 ml deionized water. The mixture was stirred at room temperature for 25 minutes, then the solvent was removed in vacuo and the residue was dissolved in 2.0 ml of methylene chloride. Purification by MPLC (column length 30 mm, I.D. 15 mm, flow 15 ml/min) using 25, 25 and 25 ml of 9:1, 8:2, 7:3 methanol/ammonia as the eluent gave 15.4 mg of the product as an off-white solid. TLC $R_f$ 0.88 (7:3 methylene chloride/methanol).

Immobilization of Anti-H1 Antibody

Monoclonal anti-H1 IgG-antibody (Biacore AB, Uppsala, Sweden) (Mw about 150,000) was immobilized to a sensor chip CM5 (Biacore AB) with EDC, NHS and ethanolamine according to the manufacturer's instructions by injection 35 μl of anti-H1 antibody diluted to 50 μg/ml in 10 mM acetate buffer, pH 5.0. A response of about 12,000 RU was obtained.

Competitive Assay Studies

Figure 5:
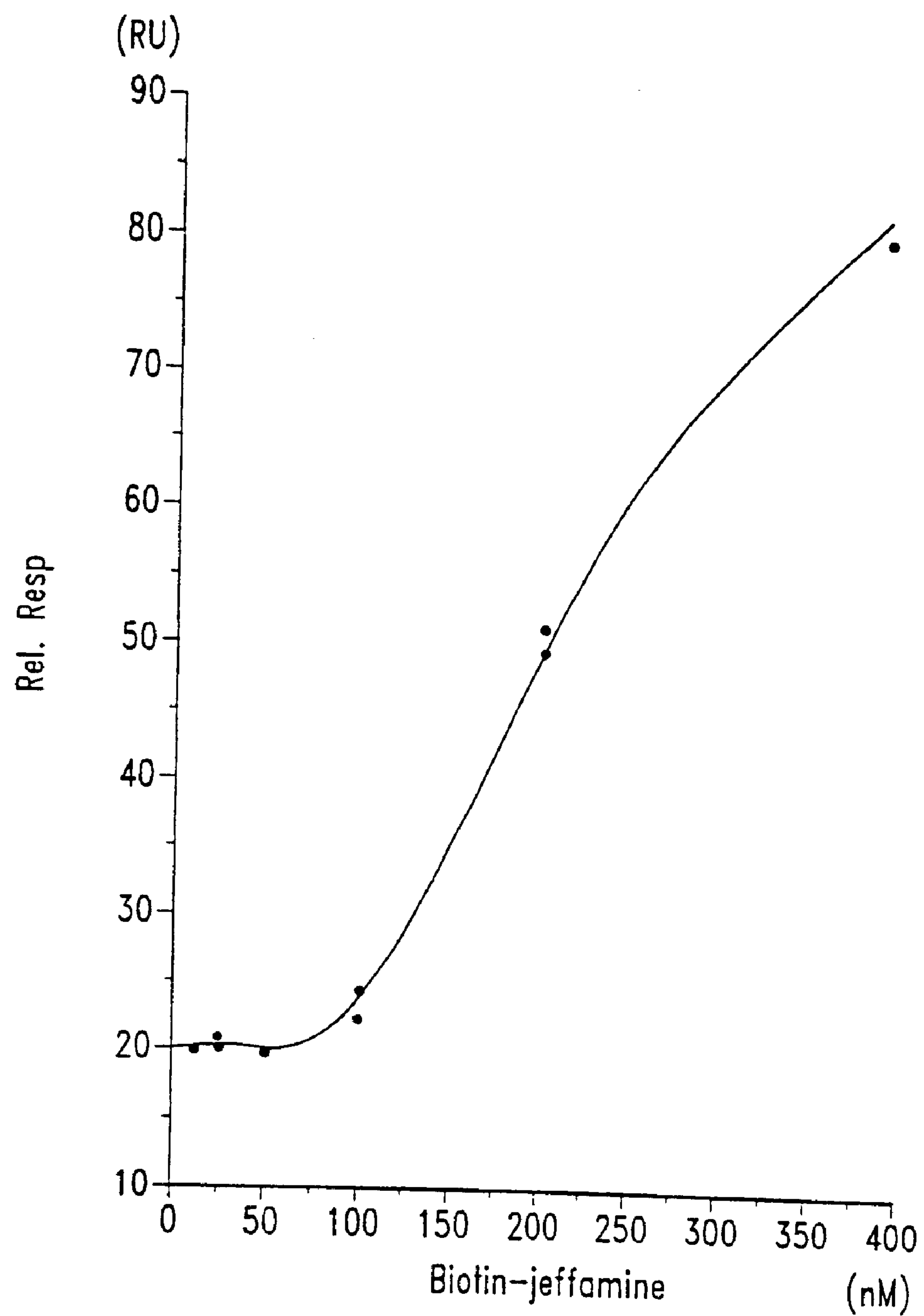
FIG. 5 is an inhibition curve for SPR response versus concentration of Biotinjeffamine obtained in a method embodiment of the invention.

Streptavidin modified magnetic particles (Dynabeads M-280 streptavidin, DYNAL) (diameter of 2.8 μm) in suspension were transferred to HBS buffer according to the manufacturer's instructions. The bead suspension (final concentration 0.3 mg/ml) was mixed wtih m-PEG-LC-biotin-JA-H1 (final concentration 0.3 μM) and the model analyte biotinjeffamine in different concentrations from 0–400 nM in the drive buffer HBS. The mixture was incubated in room temperature for 30 minutes. The beads were allowed to sediment in the sample vial, whereafter the solutions were injected over the CM5 surface with immobilized anti-H1 for four minutes. From the sensorgrams obtained, the concentration of free biotin jeffamine in each sample was calculated. FIG. 5 shows responses of conjugate binding caused by increasing amounts of added biotinjeffamine sample. It is evident from this example that interactions between small molecules and large particles, e.g. drug candidates and receptors on cells, can be studied using the described method.

Regeneration of Sensor Surface

After each analysis the CM5 surface with immobilized anti-H1 antibody was regenerated with a one minute pulse of 10 mM glycine, pH 1.5.

What is claimed is:

1. A method of determining an analyte in a liquid sample, comprising the steps of:

a) providing a solid support having immobilized thereto one member of a specific binding pair capable of reversibly binding to the other member of the specific binding pair;

b) providing a conjugate comprising (i) the analyte, or an analyte competitor, and (ii) the other member of the specific binding pair, c) simultaneously or sequentially contacting a liquid sample containing or suspected of containing the analyte with a specific binding partner to the analyte and with the conjugate, the specific binding partner to the analyte having a molecular weight of at least five times that of the conjugate, d) contacting the reacted liquid sample with the solid support to bind reacted and unreacted conjugate to the solid support, e) determining by mass-sensing at the solid support the amount of specific binding partner to the analyte that has bound in step d) to the solid support via the conjugate to determine therefrom the analyte in the sample, and f) regenerating the solid support by subjecting a surface thereof to conditions which disrupt the binding between the members of the specific binding pair to release the conjugate from the solid support and prepare the surface for a subsequent determination.

2. A method of determining an analyte in a liquid sample, comprising the steps of:

a) providing a solid support having immobilized thereto one member of a specific binding pair capable of reversibly binding to the other member of the specific binding pair, b) providing a conjugate between (i) the analyte, or an analyte competitor, and (ii) the other member of the specific binding pair, c) contacting the conjugate with the solid support to bind the conjugate thereto, d) contacting a liquid sample containing or suspected of containing the analyte with a specific binding partner to the analyte, the specific binding partner to the analyte having a molecular weight of at least five times that of the conjugate, e) contacting the reacted liquid sample with the solid support having the conjugate immobilized thereto to bind unreacted specific binding partner to the analyte, f) determining by mass-sensing at the solid support the amount of the specific binding partner to the analyte that has bound in step e) to the solid support via the conjugate to determine therefrom the analyte in the sample, and g) regenerating the solid support by subjecting a surface thereof to conditions which disrupt the binding between the members of the specific binding pair to release the conjugate from the solid support and prepare the surface for a subsequent determination.

3. A method of determining an analyte in a liquid sample, comprising the steps of:

a) providing a solid support having immobilized thereto one member of a specific binding pair capable of reversibly binding to the other member of the specific binding pair, b) providing a conjugate between (i) the analyte, or an analyte competitor, and (ii) the other member of the specific binding pair, c) simultaneously or sequentially contacting a liquid sample containing or suspected of containing the analyte with a specific binding partner to the analyte and with the conjugate, d) contacting the reacted liquid sample with the solid support to bind reacted and unreacted conjugate to the solid support, e) contacting the solid support from step d) with a reagent which specifically binds to the specific binding partner to the analyte, the reagent having a molecular weight of at least five times that of a complex between the specific binding partner to the analyte and the conjugate, f) determining by mass-sensing at the solid support the amount of the reagent that has bound to the specific binding partner to the analyte bound to the solid support via the conjugate to determine therefrom the analyte in the sample, and g) regenerating the solid support by subjecting a surface thereof to conditions which disrupt the binding between the members of the specific binding pair to release the conjugate from the solid support and prepare the surface for a subsequent determination.

4. A method of determining an analyte in a liquid sample, comprising the steps of:

a) providing a solid support having immobilized thereto one member of a specific binding pair capable of reversibly binding to the other member of the specific binding pair, b) providing a conjugate between (i) the analyte, or an analyte competitor, and (ii) the other member of the specific binding pair, c) contacting the conjugate with the solid support to bind the conjugate thereto, d) contacting the liquid sample containing or suspected to containing the analyte with a specific binding partner to the analyte, e) contacting the reacted liquid sample with the solid support to bind the unreacted specific binding partner to the analyte to the conjugate immobilized on the solid support, f) contacting the solid support with a reagent which specifically binds to the specific binding partner to the analyte, the reagent having a molecular weight of at least five times that of a complex between the specific binding partner to the analyte and the conjugate, g) determining by mass-sensing at the solid support the amount of the reagent that has bound in step f) to the specific binding partner to the analyte bound to the solid support via the conjugate to determine therefrom the analyte in the sample, and h) regenerating the solid support by subjecting a surface thereof to conditions which disrupt the binding between the members of the specific binding pair to release the conjugate from the solid support and prepare the surface for a subsequent determination.

5. A method of determining an analyte in a liquid sample, comprising the steps of:

a) providing a solid support having immobilized thereto one member of a first specific binding pair capable of reversibly binding to the other member of the first specific binding pair, b) providing a conjugate comprising (i) the analyte, or an analyte competitor, (ii) the other member of the first specific binding pair, and (iii) one member of a second specific binding pair capable of binding to the other member of the second specific binding pair, c) simultaneously or sequentially contacting a liquid sample containing or suspected of containing the analyte with a specific binding partner to the analyte and with the conjugate, d) contacting the reacted liquid sample with the solid support to bind unreacted conjugate to the solid support, complex formation between the conjugate and specific binding partner to the analyte preventing the conjugate from binding to the solid support, e) contacting the solid support with the other member of the second specific binding pair to permit the same to bind to the conjugate, the other member of the second specific binding pair having a molecular weight of at least five times that of the conjugate, f) determining by mass-sensing at the solid support the amount of the other member of the second specific binding pair that has bound in step e) to the conjugate bound to the solid support to determine therefrom the analyte in the sample, and g) regenerating the solid support by subjecting a surface thereof to conditions which disrupt the binding between the members of the first specific binding pair to release the conjugate from the solid support and prepare the surface for a subsequent determination.

6. A method of determining an analyte in a liquid sample, comprising the steps of:

a) providing a solid support having immobilized thereto one member of a first specific binding pair capable of reversibly binding to the other member of the first specific binding pair, b) providing a conjugate comprising (i) the analyte, or an analyte competitor, (ii) the other member of the first specific binding pair, and (iii) a carrier having a molecular weight of at least 5,000 Daltons, c) simultaneously or sequentially contacting a liquid sample containing or suspected of containing the analyte with a specific binding partner to the analyte and with the conjugate, d) contacting the reacted liquid sample with the solid support to bind unreacted conjugate to the solid support, complex formation between the conjugate and the specific binding partner to the analyte preventing the conjugate from binding to the solid support, e) determining by mass-sensing at the solid support the amount of the conjugate that has bound in step d) to the solid support to determine therefrom the analyte in the sample, and f) regenerating the solid support by subjecting a surface thereof to conditions which disrupt the binding between the members of the first specific binding pair to release the conjugate from the solid support and prepare the surface for a subsequent determination.

7. The method according to claim 1 or 2, wherein the specific binding partner to the analyte has a molecular weight of at least 10 times that of the conjugate.

8. The method according to claim 1 or 2, wherein the specific binding partner to the analyte has a molecular weight of at least 25 times that of the conjugate.

9. The method according to claim 1, wherein the concentration of the analyte is determined.

10. The method according to claim 1, wherein the affinity of the analyte towards the specific binding partner to the analyte is determined.

11. The method according to claim 1 or 5, wherein the first, the second or both the first and second specific binding pairs is antibody-hapten, with the hapten being part of the conjugate.

12. The method according to claim 1 or 5, wherein the first, the second or both the first and second specific binding pairs is oligonucleotide-oligonucleotide.

13. The method according to claim 3 or 4, wherein the reagent has a molecular weight of at least 10 times that of the complex between the specific binding partner to the analyte and the conjugate.

14. The method according to claim 3 or 4, wherein the reagent has a molecular weight of at least 25 times that of the complex between the specific binding partner to the analyte and the conjugate.

15. The method according to claim 6, wherein the carrier has a molecular weight of at least 10,000 Daltons.

16. The method according to claim 5, wherein the other member of the second specific binding pair has a molecular weight of at least 10 times that of the conjugate.

17. The method according to claim 5, wherein the other member of the second specific binding pair has a molecular weight of at least 25 times that of the conjugate.

18. The method according to claim 5, wherein the specific binding partner to the analyte is supported on a solid phase surface, or on a particulate carrier which is substantially not soluble in the sample and which is separated from the solid support having the one member of the first specific binding pair immobilized thereto.

19. The method according to claim 18, wherein the specific binding partner to the analyte is a cell receptor.

20. The method according to claim 18, wherein the specific binding partner to the analyte is at least substantially soluble in the sample, and wherein the binding of the specific binding partner to the analyte to the conjugate via the other member of the first specific binding pair also blocks the one member of the second specific binding pair of the conjugate, thereby preventing the other member of the second specific binding pair on the solid support from binding to the conjugate.

21. The method according to claim 1, 2, 3, 4, 5 or 6, wherein the mass sensing is performed by an optical internal reflection method.

22. The method according to claim 21, wherein the optical internal reflection method is selected from surface plasmon resonance (SPR) and frustrated total reflection (FTR).

23. The method according to claim 1, 2, 3, 4, 5 or 6, wherein the solid support is provided in a flow cell.

* * * * *

```
                              SEQUENCE LISTING

<160> NUMBER OF SEQ ID NOS:  2

<210> SEQ ID NO 1
<211> LENGTH: 17
<212> TYPE: DNA
<213> ORGANISM: Artificial Sequence
<220> FEATURE:
<223> OTHER INFORMATION: Biotinylated oligonucleotide prepared and
      immobilized to a stretavidin-coated sensor chip.

<400> SEQUENCE: 1

aagacactct ttctccc                                                  17


<210> SEQ ID NO 2
<211> LENGTH: 17
<212> TYPE: DNA
<213> ORGANISM: Artificial Sequence
<220> FEATURE:
<223> OTHER INFORMATION: FITC-labelled oligonucleotide

<400> SEQUENCE: 2

ttctgtgaga aagaggg                                                  17
```